US009741109B2

(12) United States Patent
Tada et al.

(10) Patent No.: US 9,741,109 B2
(45) Date of Patent: Aug. 22, 2017

(54) TIRE INNER SURFACE IMAGING METHOD AND DEVICE

(71) Applicant: The Yokohama Rubber Co., LTD., Minato-ku, Tokyo (JP)

(72) Inventors: Hirotaro Tada, Hiratsuka (JP); Masamichi Oyama, Hiratsuka (JP); Tsutomu Yamamoto, Hiratsuka (JP)

(73) Assignee: The Yokohama Rubber Co., LTD. (JP)

( * ) Notice: Subject to any disclaimer, the term of this patent is extended or adjusted under 35 U.S.C. 154(b) by 0 days.

(21) Appl. No.: 15/118,446

(22) PCT Filed: Jan. 30, 2015

(86) PCT No.: PCT/JP2015/052692
§ 371 (c)(1),
(2) Date: Aug. 11, 2016

(87) PCT Pub. No.: WO2015/122295
PCT Pub. Date: Aug. 20, 2015

(65) Prior Publication Data
US 2017/0024873 A1    Jan. 26, 2017

(30) Foreign Application Priority Data
Feb. 12, 2014   (JP) .................. 2014-024163

(51) Int. Cl.
*H04N 7/18*   (2006.01)
*G06T 7/00*   (2017.01)
(Continued)

(52) U.S. Cl.
CPC ......... *G06T 7/0004* (2013.01); *G01M 17/027* (2013.01); *G01N 21/95* (2013.01);
(Continued)

(58) Field of Classification Search
None
See application file for complete search history.

(56) References Cited

U.S. PATENT DOCUMENTS

| 4,234,256 A | 11/1980 | Yeager | |
| 6,840,097 B1 * | 1/2005 | Huber | .................. G01B 11/30 356/237.1 |

(Continued)

FOREIGN PATENT DOCUMENTS

| JP | S62-016450 | 1/1987 |
| JP | H10-0274515 | 10/1998 |

(Continued)

OTHER PUBLICATIONS

International Search Report for International Application No. PCT/JP2015/052692 dated Apr. 21, 2015, 3 pages, Japan.

*Primary Examiner* — Dakshesh Parikh
(74) *Attorney, Agent, or Firm* — Thorpe North & Western

(57) ABSTRACT

An imaging device inserted into an opening of a tire includes a light source, a mirror, and a camera and is configured so that the mirror revolves around a rotation shaft while an orientation of a surface of the mirror changes. The mirror is set in an imaging position by being revolved around the rotation shaft to be inserted into a tire cavity region. The tread inner surface of the tire is scanned with slit light by being irradiated with the slit light. During the scanning with the slit light, a line irradiation region on the tread inner surface formed through the irradiation of the slit light is imaged via the mirror by the camera from a direction tilted with respect to the tire circumferential direction, and image data is output.

16 Claims, 15 Drawing Sheets

(51) Int. Cl.
*G01N 21/954* (2006.01)
*G01M 17/02* (2006.01)
*G01N 21/95* (2006.01)
*G02B 26/10* (2006.01)
*H04N 5/225* (2006.01)

(52) U.S. Cl.
CPC ......... *G01N 21/954* (2013.01); *G02B 26/105* (2013.01); *H04N 5/2256* (2013.01)

(56) References Cited

U.S. PATENT DOCUMENTS

| | | | |
|---|---|---|---|
| 2001/0024279 A1* | 9/2001 | Kaneko | G01M 17/027 356/601 |
| 2005/0058333 A1 | 3/2005 | Kaneko et al. | |
| 2008/0202229 A1 | 8/2008 | Maehner et al. | |
| 2009/0282905 A1 | 11/2009 | Maehner et al. | |

FOREIGN PATENT DOCUMENTS

| | | |
|---|---|---|
| JP | 2001-174224 | 6/2001 |
| JP | 2001-249012 | 9/2001 |
| JP | 2003-240521 | 8/2003 |
| JP | 2008-203258 | 9/2008 |
| JP | 2009-115512 | 5/2009 |
| JP | 2009-531690 | 9/2009 |
| JP | 2012-112838 | 6/2012 |
| WO | WO 03/071224 | 8/2003 |
| WO | WO 2007/113231 | 10/2007 |

\* cited by examiner

TIRE INNER SURFACE IMAGING METHOD AND DEVICE

FIELD OF THE TECHNOLOGY

The present technology relates to a method and device for imaging the overall inner surface of a tire.

BACKGROUND OF THE TECHNOLOGY

When inspecting a tire's appearance, an inspector inspects outer side surfaces (outer surfaces) and inner side surfaces (inner surfaces) of all tires on the basis of a tactile sensation when touching the surfaces by hand as well as visually. For such an inspection of a tire inner surface, various methods and devices have been proposed for carrying out the inspection automatically using cameras, laser displacement gauges, or the like to measure the luminance, shape, and the like of the tire inner surface without making contact therewith.

For example, a tire inspection device disclosed in Japanese Unexamined Utility Model Registration Application Publication No. 1987-016450 inspects the position and depth of a separation in a tire inner surface through dual-exposure holographic interferometry using a laser. This configuration efficiently and clearly detects a separation in a tire, which not only contributes to quality control for tires but also ensures that retreading processes can be carried out precisely.

A tire inspection device disclosed in Japanese Unexamined Patent Application Publication No. 2012-112838 includes an inspection unit including an illumination unit, a camera, and a reflective mirror curving along an inner circumferential surface of a tire, and a drive unit that rotates the tire and the inspection unit relative to each other around an axis of the tire. With this inspection device, a photographing unit captures light from the inner circumferential surface of the tire, the light being reflected by the mirror, while rotating the tire and the inspection unit relative to each other. This allows an upper half part and a lower half part of the tire in a tire width direction to be simultaneously imaged by two imaging units.

A tire testing device disclosed in Japanese Unexamined Patent Application Publication No. 2008-203258 includes a measurement unit including at least three measurement heads, and each of the measurement heads has an illumination member and a shearing member. The first and second measurement heads scan an outer side surface of a tire's side wall. The third measurement head scans at least an inner side surface of a tread area. The use of this device enables a tire to be tested quickly and fully.

An appearance/shape inspection device for an inspection subject disclosed in Japanese Unexamined Patent Application Publication No. 2003-240521 images a tire placed on a rotating table while rotating the tire, using a light projection means that illuminates white slit light and a color charge-coupled-device (CCD) camera that images an area irradiated with the slit light. Furthermore, coordinates and luminance of the tire are detected from image data obtained by a coordinate calculating means and a luminance calculating means. Three-dimensional coordinate data and a color image of the tire are reconstructed from obtained shape data and luminance data of the tire.

An appearance and shape inspection device for an inspection subject disclosed in Japanese Unexamined Patent Application Publication No. 2001-249012 obtains appearance data generated by a first imaging means imaging a line area formed by irradiating a tire, which is an inspection subject, with first slit light, and obtains shape data generated by a second imaging means imaging the same line area at a predetermined angle of tilt, by using second slit light with which the line area is irradiated. Furthermore, the quality of the appearance is determined from the appearance data, and the quality of the shape is determined from the shape data.

An article inspection method disclosed in Japanese Unexamined Patent Application Publication No. 2009-115512 determines the quality of an appearance on the basis of image data generated with a rotating table that holds a tire, an irradiation means that irradiates a tire inner surface with a line-form laser beam, and a camera that is attached to a robot hand and images the tire inner surface.

However, problems with mechanisms that measure the inner side of a tire includes the space in a tire inner side, corresponding to a tire cavity region filled with air when the tire is assembled on a rim, being narrow, and the dimensions of areas to be measured varying depending on the size of the tire. Therefore, because the size of an imaging unit that can be inserted into the space on the tire inner side is limited, and the tire inner side curves greatly in the tire width direction, it is necessary to divide the tire inner surface into two side inner surfaces and a tread inner surface in order to image the overall tire inner surface with the above-described conventional devices or methods. For example, it is necessary to image one side inner surface of the tire, the other side inner surface, and the tread inner surface separately, or to image both of the side inner surfaces of the tire and the tread inner surface separately. As a result, the man-hours involved in the imaging increase, and it takes time to image a single tire inner surface.

SUMMARY OF TECHNOLOGY

The present technology provides a tire inner surface imaging method and device that can image a tire inner surface in a short amount of time even for tires having a variety of outer diameters.

One aspect of the present technology is a tire inner surface imaging method for imaging a tire inner surface. This method includes the steps of:

setting a mirror in an imaging position by revolving the mirror around a rotation shaft so that the mirror is inserted into a tire cavity region with a portion of an imaging device inserted into an opening of a tire, the imaging device including a light source, the mirror, and a camera and being configured so that the mirror revolves around the rotation shaft while an orientation of a surface of the mirror changes;

scanning a tread inner surface of the tire with slit light by irradiating the tread inner surface with the slit light; and outputting image data generated by the camera imaging a line irradiation region on the tread inner surface from a direction tilted with respect to a tire circumferential direction via the mirror during the scanning with the slit light, the line irradiation region being formed through the irradiation of the slit light.

A rotation amount of the rotation shaft, when the mirror is inserted into the tire cavity region, is determined according to an outer diameter of the tire so that an angle of tilt of the imaging performed by the camera is within an acceptable range.

It is preferable that the camera be a fixed focus camera, and that a mechanism that changes a distance of an optical path between the mirror and the camera be provided.

It is preferable that the step of setting the mirror in the imaging position include revolving the mirror to the imaging position according to the rotation amount determined for the mirror, from a position in which the mirror is located so that an outer circumference of a portion of the imaging device to be inserted into the opening is smaller than an inner circumference of the tire.

It is preferable that a sub-mirror be provided in an optical path, between the camera and the mirror, of light reflected from the line irradiation region, the sub-mirror being configured to direct light reflected by the mirror toward a light-receiving surface of the camera.

It is preferable that the imaging device include a side inner surface imaging optical system besides a tread inner surface imaging optical system that includes the light source, the mirror, and the camera as a tread inner surface light source, a tread inner surface mirror, and a tread inner surface camera, respectively, the side inner surface imaging optical system configured to output image data generated by a side inner surface camera imaging, from a direction tilted in the tire circumferential direction via a side inner surface mirror, a line irradiation region formed by irradiating a side inner surface of the tire inner surface with slit light emitted from a side inner surface light source, the side inner surface mirror being configured to revolve around a side inner surface rotation shaft while an orientation of the side inner surface mirror changes, and the step of setting the mirror in the imaging position including revolving the side inner surface mirror so that the side inner surface mirror is inserted into the tire cavity region.

A more specific aspect of the present technology is the following tire inner surface imaging method.

That is, this aspect is a tire inner surface imaging method for imaging a tire inner surface over a single pass in a circumferential direction of a tire by rotating at least the tire or an imaging device central to an axis of the tire. This tire inner surface imaging method employs an imaging device including an optical system provided for each of the portions obtained by dividing the tire inner surface into three or more portions in the tire width direction. The optical systems simultaneously irradiates the tire inner surface with slit light, images the tire inner surface irradiated with the slit light, and outputs image data. At least some of the mirrors including second mirrors of the respective optical systems are inserted into the tire cavity region. In each of the optical systems, when the at least some of the mirrors including the second mirrors are inserted into the tire cavity region, the positions of the mirrors are changed so that an outer circumference of the portion to be inserted becomes smaller than an inner circumference of the tire. After the insertion, the positions of the mirrors are changed to positions suited to imaging. Thereafter, the slit light is emitted from the light sources, the slit light emitted from the light sources is reflected by first mirrors, and the optical systems irradiate the corresponding portions of the tire inner surface so that a plane of the reflected slit light extends in the tire width direction. The slit light with which the tire inner surface is irradiated from the first mirrors and is reflected by the tire inner surface is incident on the second mirrors and reflected toward third mirrors, the slit light reflected by the second mirrors is reflected by the third mirrors toward incidence openings of the corresponding cameras, the cameras image the tire inner surface irradiated with the slit light by receiving the slit light reflected by the third mirrors, and the generated image data is output to the outside.

According to this tire inner surface imaging method, at least some of the mirrors including the second mirrors of the respective optical systems are inserted into the tire when the tire inner surface is imaged. Thereafter, the slit light is emitted from each of the light sources, the slit light is reflected by the first mirrors, and the slit light illuminates predetermined portions of the tire inner surface so as to extend in the tire width direction. The slit light reflected from the tire inner surface is incident on the second mirrors and is reflected toward the third mirrors. Furthermore, the slit light reflected by the second mirrors is reflected by the third mirrors toward the incidence openings of the corresponding cameras, and the tire inner surface irradiated with the slit light is imaged by the cameras. The pieces generated image data are output to the outside simultaneously.

Another aspect of the present technology is a tire inner surface imaging device for imaging a tire inner surface. The device includes:

a light source configured to irradiate a tread inner surface of a tire with slit light;

a mirror configured to reflect light reflected from a line irradiation region on the tread inner surface formed by the irradiation of the slit light;

a camera configured to output image data generated by receiving light reflected by the mirror and imaging the line irradiation region from a direction tilted in a tire circumferential direction;

an inner surface measurement stage where the light source, the mirror, the camera, and a mechanism are mounted, the mechanism being configured to revolve the mirror around a rotation shaft while changing an orientation of a surface of the mirror, the inner surface measurement stage having an outer circumference smaller than an inner circumference of an opening of the tire; and a control unit configured to control revolution of the mirror by controlling a rotation amount of the rotation shaft.

The control unit is configured to generate a control signal for the rotation amount of the rotation shaft according to an outer diameter of the tire so that, when the mirror is revolved around the rotation shaft and inserted into a tire cavity region to be set in an imaging position, an angle of tilt of the imaging of the line irradiation region performed by the camera is within an acceptable range.

It is preferable that the camera be a fixed focus camera, and a mechanism configured to move the camera so as to change a distance of an optical path between the mirror and the camera be provided.

It is preferable that the control unit use the control signal to revolve the mirror from a position in which the mirror is located so that the outer circumference of the inner surface measurement stage is smaller than an inner circumference of the tire.

It is preferable that a sub-mirror be provided in an optical path, between the camera and the mirror, of light reflected from the line irradiation region, the sub-mirror being configured to direct light reflected by the mirror toward a light-receiving surface of the camera.

It is preferable that the device include a side inner surface imaging optical system besides a tread inner surface imaging optical system that includes the light source, the mirror, and the camera as a tread inner surface light source, a tread inner surface mirror, and a tread inner surface camera, respectively, the side inner surface imaging optical system including a side inner surface light source configured to irradiate a side inner surface of the tire inner surface with slit light, a side inner surface camera configured to output image data generated by imaging a line irradiation region formed by the irradiation of the slit light, and a side inner surface mirror that is provided in an optical path of light reflected from the line irradiation region so that the side inner surface camera performs the imaging from a direction tilted in the tire circumferential direction, the side inner surface mirror being configured to revolve around a side inner surface rotation shaft while an orientation of the side inner surface mirror changes.

Additionally, a more specific aspect of the present technology is a tire inner surface imaging device configured to image a tire inner surface around the tire in a circumferential direction of a tire by rotating at least the tire or the imaging device central to an axis of the tire.

This tire inner surface imaging device includes:

an inner surface measurement stage having an outer circumference that is smaller than an inner circumference of an opening of the tire; and an optical system provided for each of the portions obtained by dividing the tire inner surface into three or more portions in a width direction, the optical systems being provided on the inner surface measurement stage and simultaneously configured to irradiate the tire inner surface with slit light, image the tire inner surface irradiated with the slit light, and output image data.

Each of the optical systems includes:

a light source configured to emit the slit light;

a first mirror configured to reflect the slit light emitted from the light source, and irradiate a portion of the tire inner surface that the optical system is responsible for so that a plane of the reflected slit light extends in the tire width direction;

a second mirror on which the slit light that illuminates the tire inner surface from the first mirror and that is reflected by the tire inner surface is configured to be incident, and that is configured to reflect the slit light toward a third mirror;

the third mirror configured to reflect the slit light reflected by the second mirror toward an incidence opening of a camera;

the camera configured to receive the slit light reflected by the third mirror, image the tire inner surface irradiated with the slit light, and output the generated image data to the outside; and a means for changing a position of the second mirrors of the respective optical systems so that when at least some of the mirrors including the second mirrors are inserted into the tire along with the inner surface measurement stage, an outer circumference of the portion to be inserted is smaller than an inner circumference of the opening of the tire.

According to the tire inner surface imaging device of the above-described aspect, at least part of each of the optical systems including the second mirror is inserted into the tire along with the inner surface measurement stage when the tire inner surface is imaged. Thereafter, the slit light is emitted from each of the light sources, the slit light is reflected by the first mirrors and illuminates a predetermined portion of the tire inner surface so as to extend in the tire width direction. The slit light reflected from the tire inner surface is incident on the second mirrors and is reflected toward the third mirrors. Furthermore, the slit light reflected by the second mirrors is reflected by the third mirrors toward the incidence openings of the cameras, and the tire inner surface irradiated with the slit light is imaged by the cameras. The pieces of generated image data are output to the outside simultaneously.

According to the above-described tire inner surface imaging method and device, a rotation amount of a rotation shaft for revolving a mirror is set according to an outer diameter of a tire, and thus the tire inner surface can be imaged in a short amount of time even for tires having a variety of outer diameters. Additionally, in the case of a configuration in which an optical system is provided for each of the portions obtained by dividing the tire inner surface into three or more portions in a width direction, the entire tire inner surface can be imaged over a single pass in a circumferential direction of the tire by rotating at least the tire or the imaging device central to a central axis of rotation of the tire. Accordingly, the amount of time required to image the entire tire inner surface can be greatly shortened compared to conventional configurations. It is only necessary to insert the mirror of each of the optical systems into the tire cavity region, making it possible to reduce the size of the portion to be inserted into the tire cavity region compared to conventional configurations. As a result, the optical systems for imaging the entire inner surface of the tire can be driven simultaneously.

DETAILED DESCRIPTION

Figure 1:
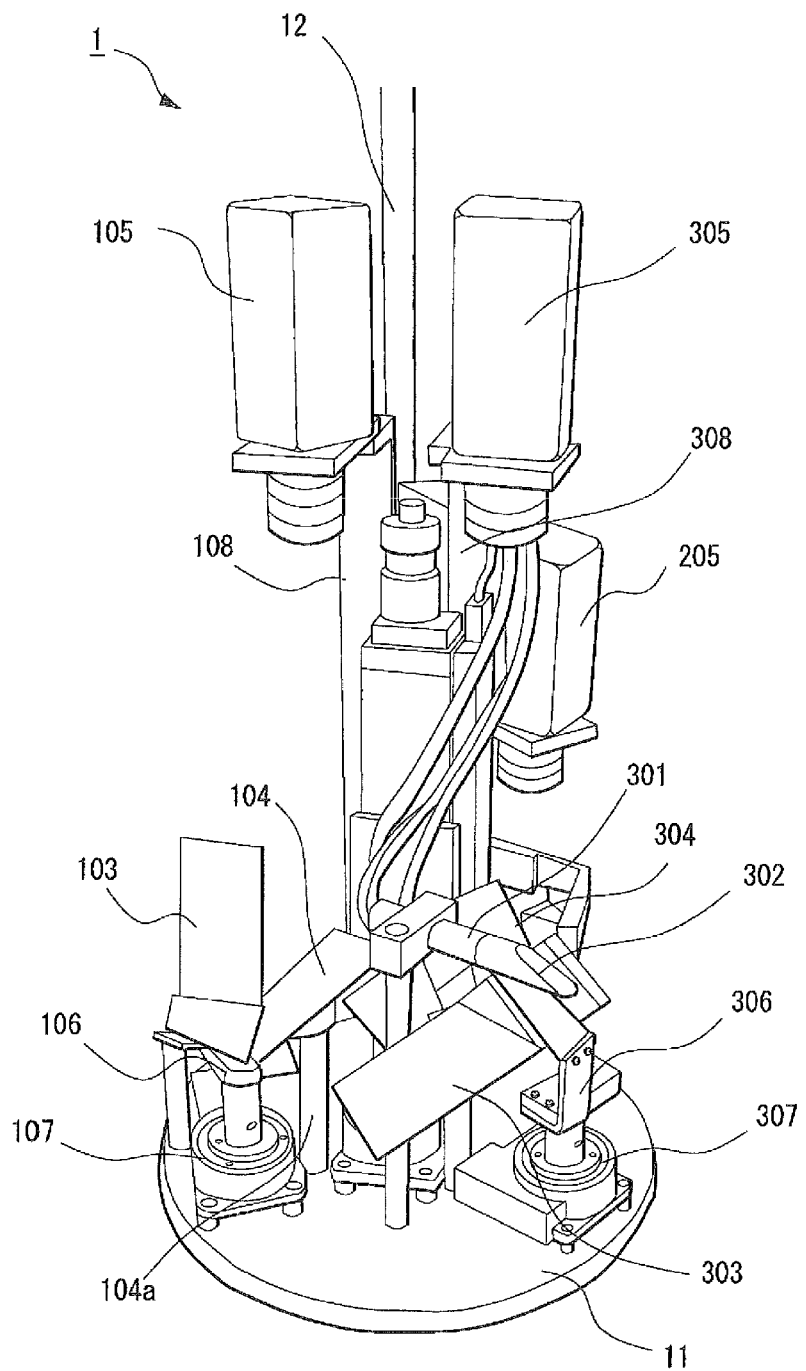
FIG. 1 is an external perspective view of the main parts of a tire inner surface imaging device according to an embodiment of the present technology.

Hereinafter, an embodiment of the present technology will be described with reference to the drawings.

In this specification, a tire cavity region refers to a region of space that is surrounded by a tire and a rim and is filled with air that is supplied into the tire assembled on the rim.

A tire inner surface refers to a part of the tire surface that faces the tire cavity region, and the tire inner surface includes a tread inner surface located in a position corresponding to a tread portion of the tire and side inner surfaces located in positions corresponding to side portions. The side inner surfaces include two surfaces corresponding to both sides of the tire. In this specification, one of these surfaces is called a side upper surface, and the other surface is called a side lower surface.

An imaging device including a tread inner surface light source, a tread inner surface mirror, and a tread inner surface camera is employed when imaging the tire inner surface according to the present embodiment. The imaging device is configured so that the tread inner surface mirror revolves around a rotation shaft while changing the orientation of a surface of the tread inner surface mirror. When imaging the tire inner surface, the imaging device is partially inserted into an opening of the tire. The opening refers to an opening part surrounded by a bead base region of the tire, and is an area where the rim is located when the tire is assembled on the rim. At this time, the above-described rotation shaft is parallel to a central axis of rotation of the tire, and the rotation shaft is inserted with the rotation shaft offset with respect to the central axis of rotation of the tire. In this state, the tread inner surface mirror is revolved and inserted into the tire cavity region to be set in an imaging position. The tread inner surface light source irradiates the tire tread inner surface with slit light to scan the tread inner surface with the slit light. During the scanning with this slit light, a line irradiation region on the tread inner surface formed by the irradiation of the slit light is imaged by the tread inner surface camera via the tread inner surface mirror from a direction tilted in the tire circumferential direction, and image data is output. When the tread inner surface mirror is inserted into the tire cavity region, the rotation amount of the rotation shaft is determined according to the outer diameter of the tire so that the tilt angle of the imaging performed by the tread inner surface camera is within an acceptable range.

In this manner, in the imaging of the tire inner surface according to the present embodiment, the rotation amount of the rotation shaft for revolving the tread inner surface mirror can be determined according to the outer diameter of the tire so that the tilt angle of the imaging performed by the tread inner surface camera is within an acceptable range, and thus stable image data can be output regardless of the outer diameter of the tire. In particular, in data processing based on the light section method, it is preferable that the tilt angle when imaging the line irradiation region be kept within an acceptable range including a constant tilt angle regardless of the outer diameter of the tire in order to maintain a constant high resolution and stably obtain highly-accurate shape data of the tire inner surface from the image data. The imaging of the tire inner surface according to the present embodiment, which can determine the rotation amount of the rotation shaft for revolving the tread imaging mirror according to the outer diameter of the tire so that the tilt angle of the imaging performed by the tread inner surface camera is within an acceptable range, is effective from this standpoint. A device and method for imaging the tire inner surface will be described in detail hereinafter.

Figure 2:
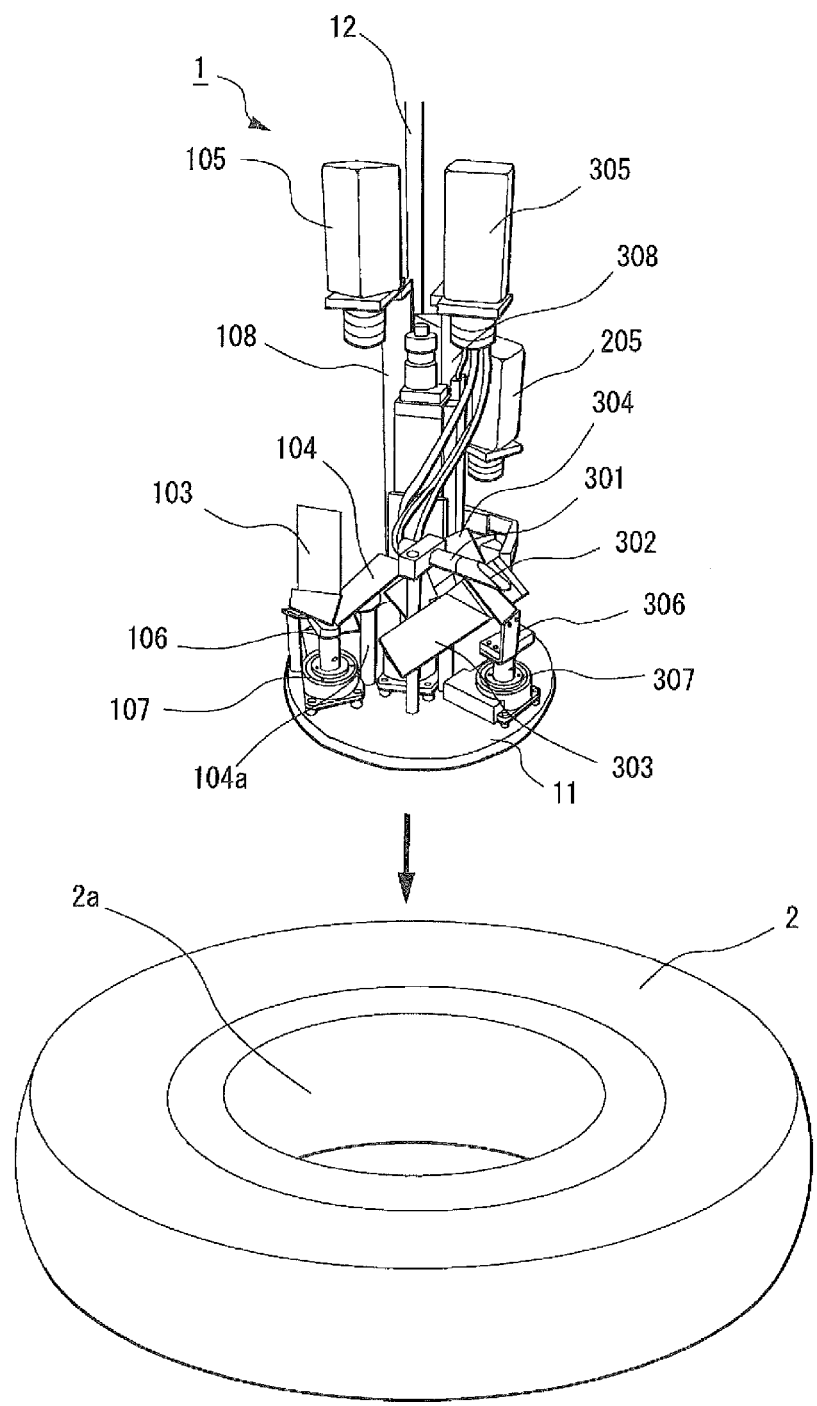
FIG. 2 is a diagram illustrating a positional relationship between the tire inner surface imaging device and a tire according to the embodiment of the present technology.

As illustrated in FIGS. 1 to 6, a tire inner surface imaging device 1 according to the present embodiment includes a circular plate-shaped or substantially circular plate-shaped inner surface measurement stage 11 and a support column 12 affixed, in an upright position, to the center of an upper surface of the inner surface measurement stage 11. Cuts are formed in the inner surface measurement stage 11 at substantially every 120 degrees along the outer circumference of the stage, dividing the stage into three regions, namely a first region, a second region, and a third region. An optical system for imaging a corresponding tire inner surface is mounted in each of these regions. When the tire inner surface is imaged, as illustrated in FIG. 2, the inner surface measurement stage 11 is inserted into a tire 2 from an opening 2a. The outer circumference of the inner surface measurement stage 11 is smaller than the inner circumference of the opening 2a, or in other words, is smaller than the inner circumference of a bead base region of the tire, so that the inner surface measurement stage 11 can be inserted into the opening 2a at this time. Therefore, in the present embodiment, the mirrors to be inserted into the tire cavity region when the tire inner surface is imaged are revolvable.

First, the optical systems of the device 1 will be described.

Figure 4:
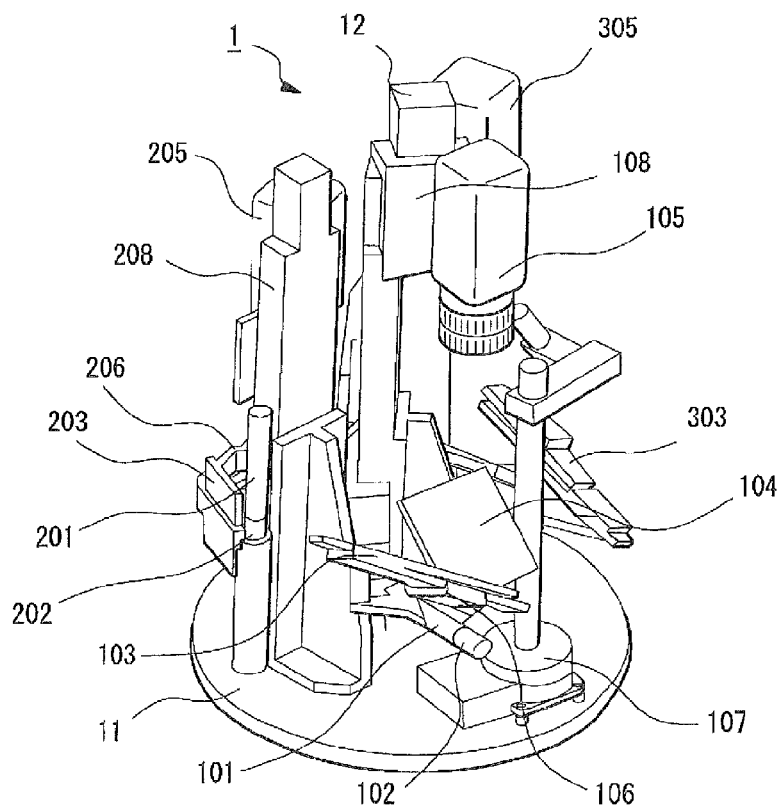
FIG. 4 is an external perspective view illustrating a state in which the mirrors are retracted in the tire inner surface imaging device according to the embodiment of the present technology.

A first optical system 100 for imaging the side upper surface within the tire 2 is provided in the first region. As illustrated in FIG. 4, the first optical system 100 includes a light source 101 that emits slit light, first to third mirrors 102, 103, and 104, and a camera 105. The light source 101 is a side inner surface light source that forms a line irradiation region by irradiating the side upper surface, which is one side inner surface, with the slit light.

The first mirror 102 is affixed to a tip portion of the light source 101. The first mirror 102 reflects the slit light emitted from the light source 101 so that an angle of incidence of the slit light incident on the side upper surface within the tire 2 is a right angle relative to the tire circumferential direction, and so that the slit light illuminates the surface having been spread out in the width direction of the tire. The first mirror 102 is positioned within the outer circumference of the inner surface measurement stage 11.

Figure 3:
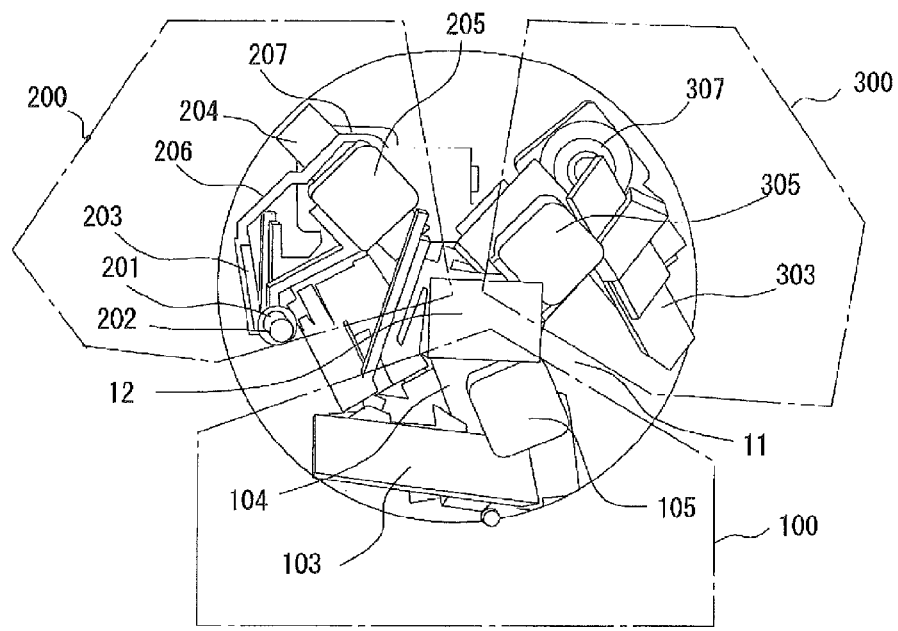
FIG. 3 is a plan view illustrating a state in which mirrors are retracted in the tire inner surface imaging device according to the embodiment of the present technology.
Figure 5:
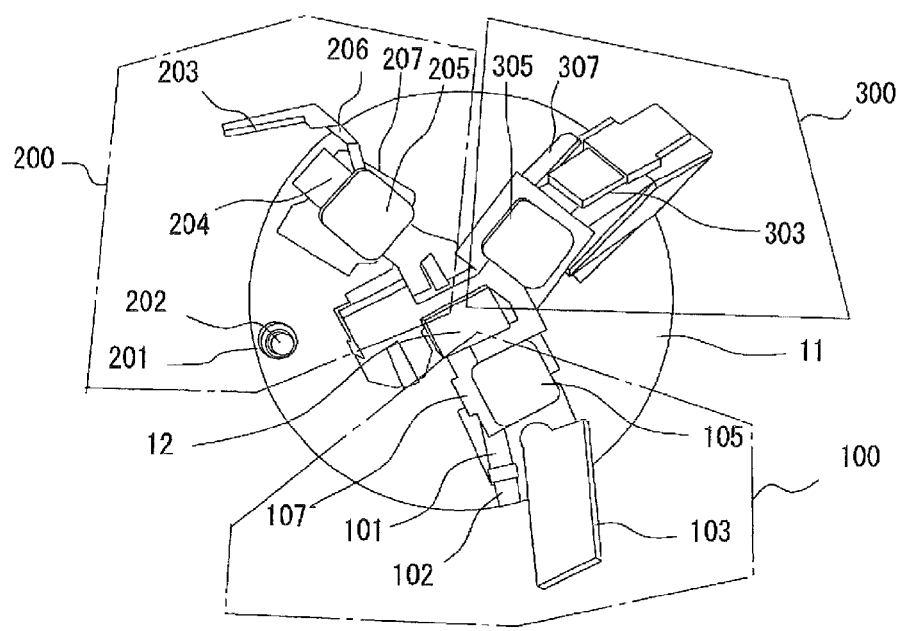
FIG. 5 is a plan view illustrating a state in which mirrors are extended in the tire inner surface imaging device according to the embodiment of the present technology.
Figure 6:
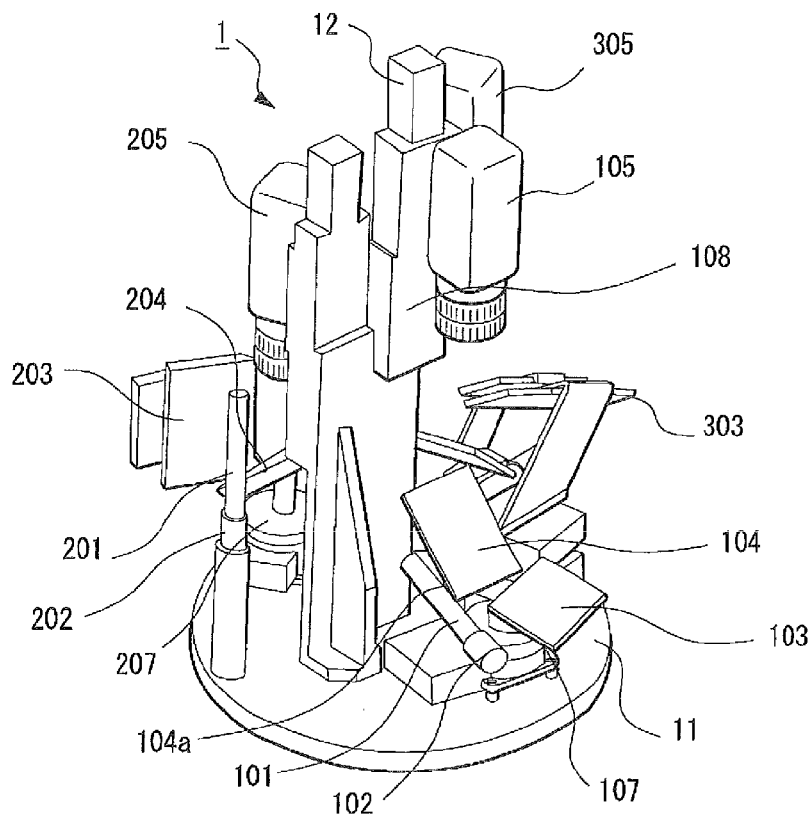
FIG. 6 is an external perspective view illustrating a state in which mirrors are extended in the tire inner surface imaging device according to the embodiment of the present technology.
Figure 7:
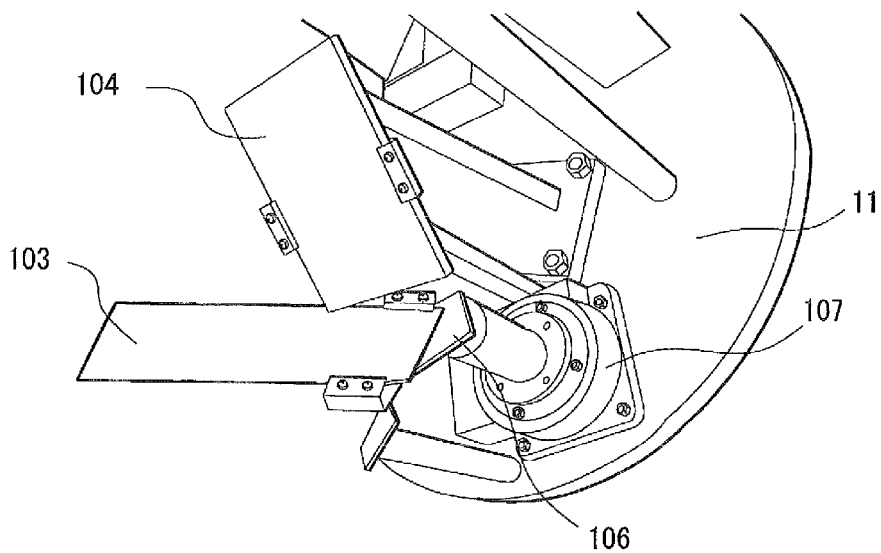
FIG. 7 is an external perspective view illustrating a state in which a mirror of a first optical system is retracted, according to the embodiment of the present technology.
Figure 8:
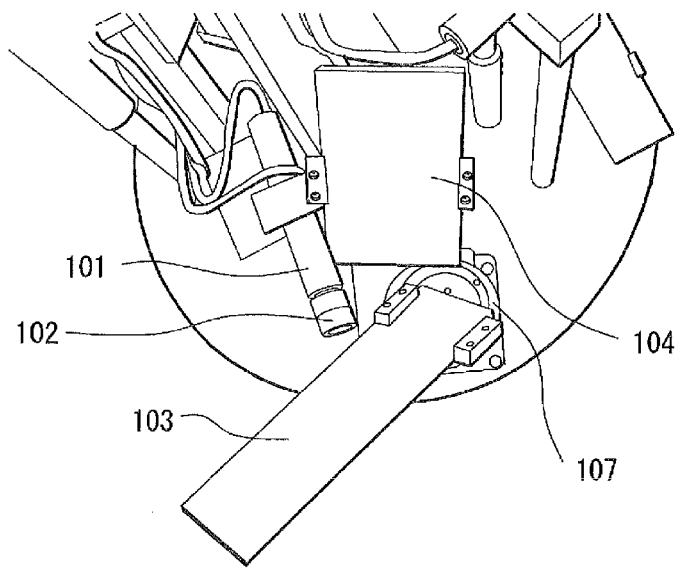
FIG. 8 is an external perspective view illustrating a state in which the mirror of the first optical system is extended, according to the embodiment of the present technology.

The second mirror 103 is affixed to one end side of a support member 106, and the other end side of the support member 106 is connected to a rotational driving mechanism unit 107. This configuration enables the second mirror 103 to revolve around a rotation shaft of the rotational driving mechanism unit 107. As the mirror revolves in this manner, the orientation of the mirror also changes. The second mirror 103 is a side inner surface mirror that, when the camera 105 images the line irradiation region irradiated with the slit light, reflects reflected slit light from the line irradiation region and guides that reflected light to the camera 105 so that imaging is carried out from a direction tilted in the tire circumferential direction. Rotation of a stepping motor of the rotational driving mechanism unit 107 rotates the support member 106 and the second mirror 103 central to a rotation shaft perpendicular to the upper surface of the inner surface measurement stage 11. The second mirror 103 revolves around the above-described rotation shaft in this manner. The revolution of the second mirror 103 is controlled by a computer device, which will be described later, so that the second mirror 103 is located in a predetermined position within the outer circumference of the inner surface measurement stage 11 when imaging is not being carried out, as illustrated in FIGS. 3, 4, and 7, and so that the second mirror 103 is located in a position that is outside of the outer circumference of the inner surface measurement stage 11 and where the reflected light from the side upper surface of the tire can be received (an imaging position) during imaging, as illustrated in FIGS. 5, 6, and 8. The second mirror 103 is positioned within the tire cavity region in the case where the second mirror 103 is positioned outside of the outer circumference of the inner surface measurement stage 11.

The third mirror 104 is affixed by a support member 104a to a position, within the outer circumference of the inner surface measurement stage 11, where reflected slit light that has been reflected by the second mirror 103 can be reflected toward an incidence opening and furthermore a light-receiving surface of the camera 105. The third mirror 104 is a sub-mirror that is provided within an optical path of reflected light from the line irradiation region, between the camera 105 and the second mirror 103, and that directs the light reflected by the second mirror 103 toward the incidence opening and furthermore the light-receiving surface of the camera 105.

The camera 105 is attached, via a mobile mechanism unit 108, to an anchor column affixed perpendicular to the inner surface measurement stage 11.

The camera 105 is a side inner surface camera that images the line irradiation region on the tread inner surface from a direction tilted in the tire circumferential direction via the second mirror 103 and outputs image data. Additionally, the camera 105 includes a fixed focus lens, and the focus of the image of the line irradiation region is adjusted by varying a distance along the optical path between the lens of the camera 105 and the third mirror 104, and furthermore, the second mirror 103, using the mobile mechanism unit 108 along the anchor column. The mobile mechanism unit 108 is operated by a stepping motor, and the driving of the stepping motor is controlled by the computer device, which will be described later.

A second optical system 200 for imaging the tread inner surface within the tire 2 is provided in the second region. The second optical system 200 includes a light source 201 that emits slit light, first to third mirrors 202, 203, and 204, and a camera 205.

The light source 201 is a tread inner surface light source that forms a line irradiation region by irradiating the tread inner surface with the slit light.

The first mirror 202 is affixed to a tip portion of the light source 201. The first mirror 202 reflects the slit light emitted from the light source 201 so that an angle of incidence of the slit light incident on the tread inner surface within the tire 2 is a right angle relative to the tire circumferential direction, and so that the slit light illuminates the surface having been spread out in the width direction of the tire. The first mirror 202 is positioned within the outer circumference of the inner surface measurement stage 11.

Figure 9:
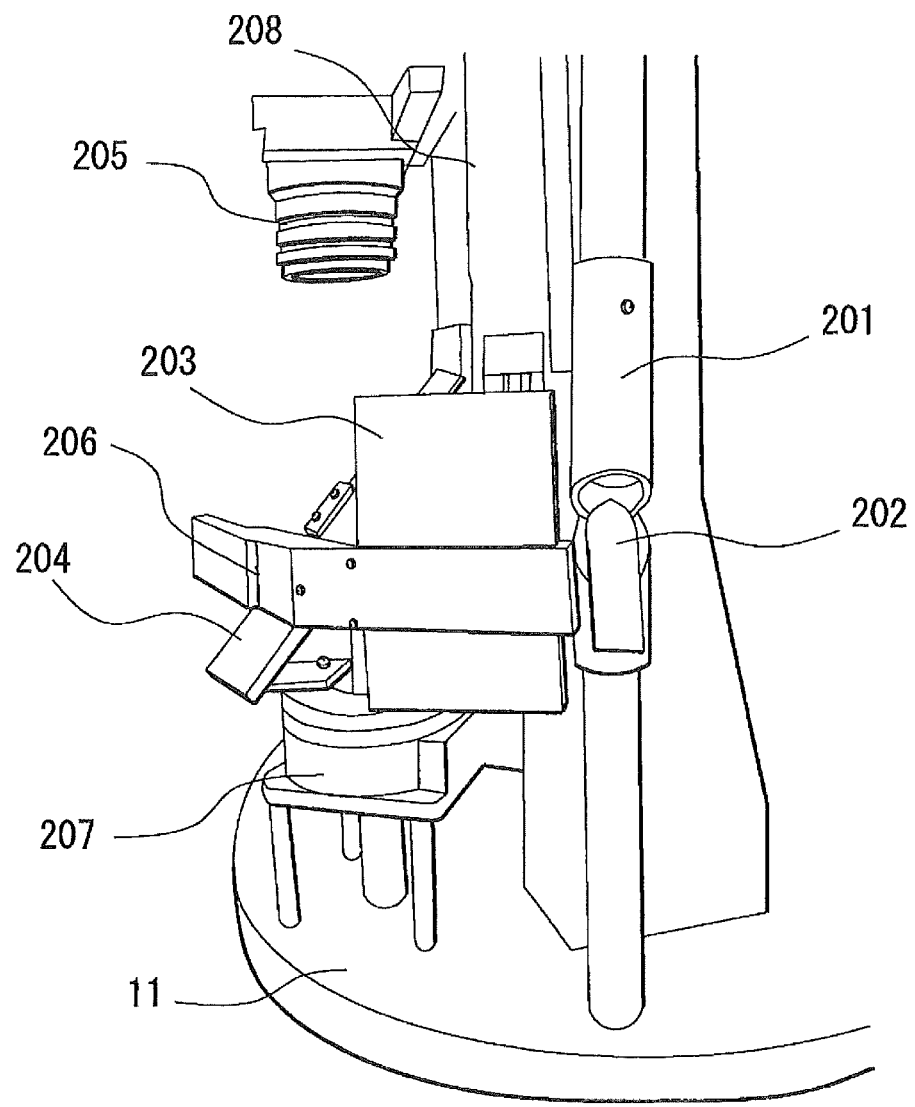
FIG. 9 is an external perspective view illustrating a state in which a mirror of a second optical system is retracted, according to the embodiment of the present technology.
Figure 10:
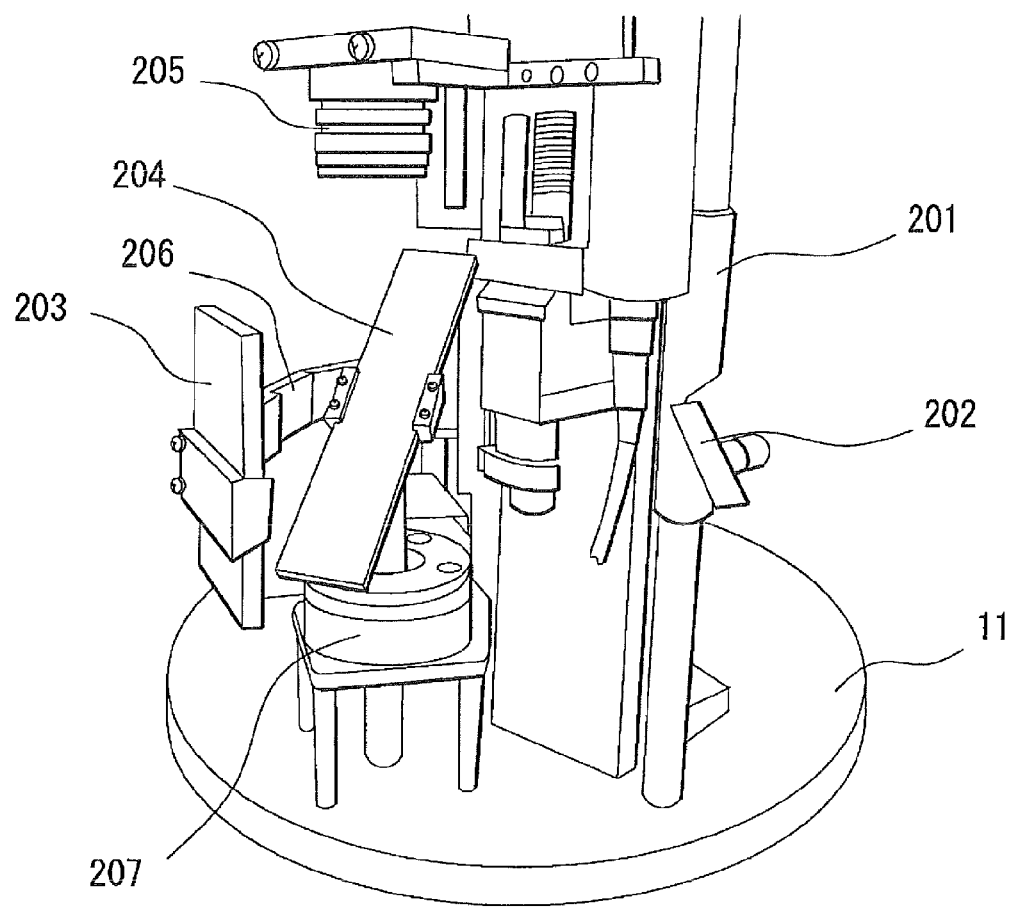
FIG. 10 is an external perspective view illustrating a state in which the mirror of the second optical system is extended, according to the embodiment of the present technology.
Figure 11:
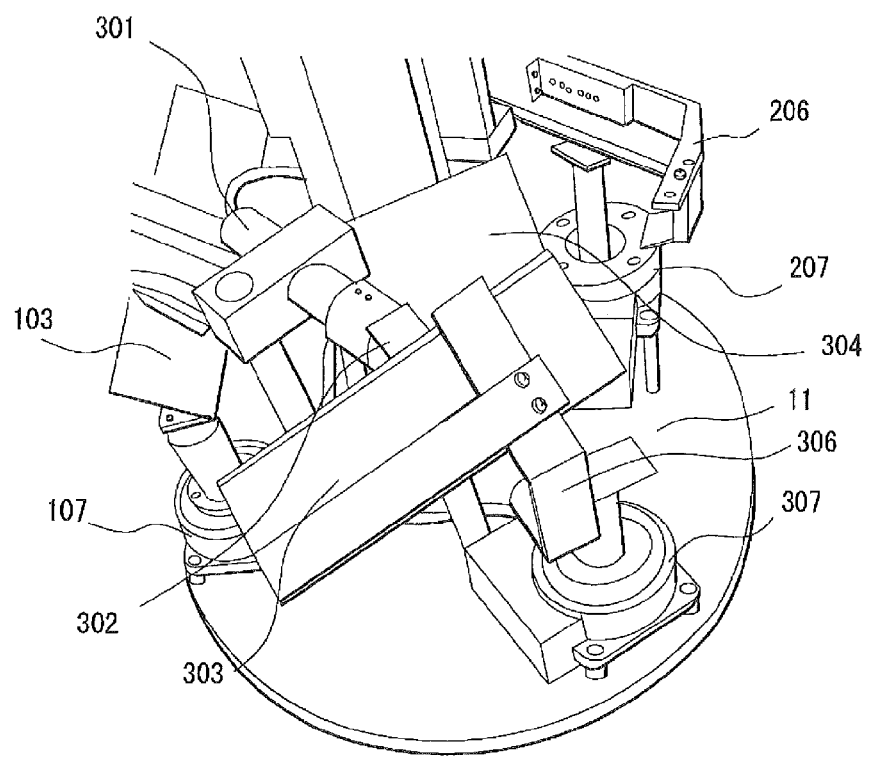
FIG. 11 is an external perspective view illustrating a state in which a mirror of a third optical system is retracted, according to the embodiment of the present technology.
Figure 12:
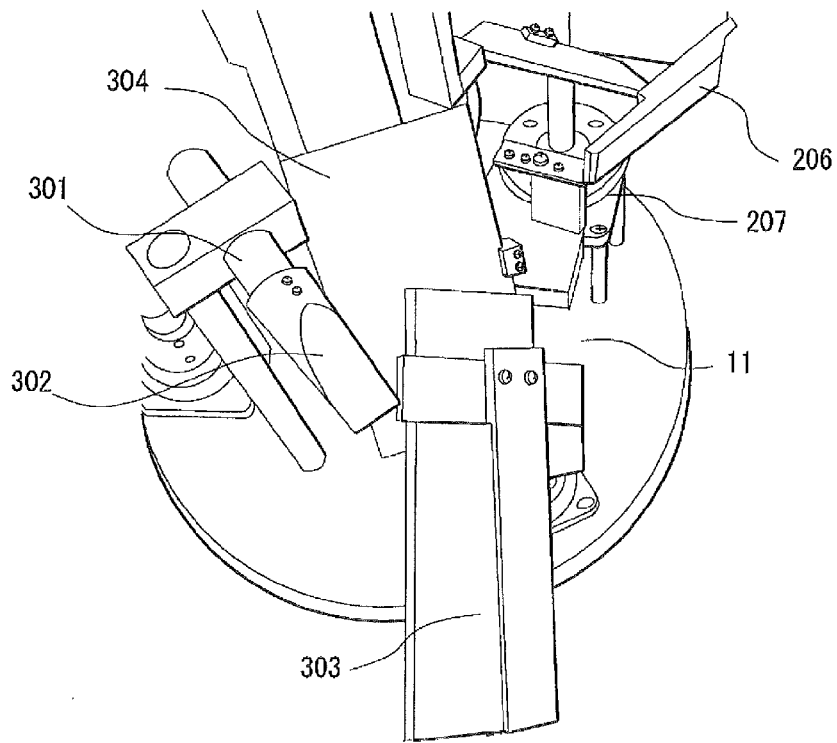
FIG. 12 is an external perspective view illustrating a state in which the mirror of the third optical system is extended, according to the embodiment of the present technology.

The second mirror 203 is affixed to one end side of a support member 206, and the other end side of the support member 206 is connected to a rotational driving mechanism unit 207. This configuration enables the second mirror 203 to revolve around a rotation shaft of the rotational driving mechanism unit 207. As the mirror revolves in this manner, the orientation of the mirror also changes. The second mirror 203 is a tread inner surface mirror that, when the camera 205 images the line irradiation region, reflects reflected light from the line irradiation region and guides that reflected light to the camera 205 so that imaging is carried out from a direction tilted in the tire circumferential direction. As a result, rotation of a stepping motor of the rotational driving mechanism unit 207 rotates the support member 206 and the second mirror 203 central to a rotation shaft perpendicular to the upper surface of the inner surface measurement stage 11. The second mirror 203 revolves around the above-described rotation shaft in this manner. The revolution of the second mirror 203 is controlled by a computer device, which will be described later, so that the second mirror 203 is located in a predetermined position within the outer circumference of the inner surface measurement stage 11 when imaging is not being carried out, as illustrated in FIGS. 3, 4, and 9, and so that the second mirror 203 is located in a position that is outside of the outer circumference of the inner surface measurement stage 11 and where the reflected light from the side upper surface of the tire can be received (an imaging position) during imaging, as illustrated in FIGS. 5, 6, and 10. The second mirror 203 is positioned within the tire cavity region in the case where the second mirror 203 is positioned outside of the outer circumference of the inner surface measurement stage 11.

The third mirror 204 is affixed by a support member 204a to a position, within the outer circumference of the inner surface measurement stage 11, where slit light that has been reflected by the second mirror 203 can be reflected toward an incidence opening and furthermore a light-receiving surface of the camera 205. The third mirror 204 is a sub-mirror that is provided within an optical path of reflected light from the line irradiation region, between the camera 205 and the second mirror 203, and directs the light reflected by the second mirror 203 toward the incidence opening and furthermore the light-receiving surface of the camera 205.

The camera 205 is attached, via a mobile mechanism unit 208, to an anchor column affixed perpendicular to the inner surface measurement stage 11. The camera 205 is a tread inner surface camera that images the line irradiation region on the tread inner surface from a direction tilted in the tire circumferential direction via the second mirror 203 and outputs image data. Additionally, the camera 205 includes a fixed focus lens, and the focus of the image of the line irradiation region is adjusted by varying a distance along the optical path between the lens of the camera 205 and the third mirror 204, and furthermore, the second mirror 203, using the mobile mechanism unit 208 along the anchor column. The mobile mechanism unit 208 operates using a stepping motor, and the driving of the stepping motor is controlled by the computer device, which will be described later. In particular, as will be described later, the revolution of the second mirror 203 is controlled according to the outer diameter of the tire, and a distance from the line irradiation region on the tread inner surface to the second mirror 203 is varied. Accordingly, it is preferable that a mechanism that varies a distance of the optical path between the camera 205 and the second mirror 203 so that a distance along an optical path of the camera 205 including the fixed focus lens to the line irradiation region is constant be included.

A third optical system 300 for imaging the side lower surface within the tire 2 is provided in the third region. The third optical system 300 includes a light source 301 that emits slit light, first to third mirrors 302, 303, and 304, and a camera 305. The light source 301 is a side inner surface light source that forms a line irradiation region by irradiating the side lower surface, which is one side inner surface, with the slit light.

The first mirror 302 is affixed to a tip portion of the light source 301. The first mirror 302 reflects the slit light emitted from the light source 301 so that an angle of incidence of the slit light incident on the side lower surface within the tire 2 is a right angle relative to the tire circumferential direction, and so that the slit light illuminates the surface having been spread out in the width direction of the tire. The first mirror 302 is positioned within the outer circumference of the inner surface measurement stage 11.

The second mirror 303 is affixed to one end side of a support member 306, and the other end side of the support member 306 is connected to a rotational driving mechanism unit 307. As a result, the second mirror 303 can revolve around a rotation shaft of the rotational driving mechanism unit 307. As the mirror revolves in this manner, the orientation of the mirror also changes. The second mirror 303 is a side inner surface mirror that, when the camera 305 images the line irradiation region, reflects reflected slit light from the line irradiation region and guides that reflected light to the camera 305 so that imaging is carried out from a direction tilted in the tire circumferential direction. Rotation of a stepping motor of the rotational driving mechanism unit 307 rotates the support member 306 and the second mirror 303 central to a rotation shaft perpendicular to the upper surface of the inner surface measurement stage 11. The second mirror 303 revolves around the above-described rotation shaft in this manner. The revolution of the second mirror 303 is controlled by a computer device, which will be described later, so that the second mirror 303 is located in a predetermined position within the outer circumference of the inner surface measurement stage 11 when imaging is not being carried out, as illustrated in FIGS. 3, 4, and 7, and so that the second mirror 303 is located in a position that is outside of the outer circumference of the inner surface measurement stage 11 and where the reflected light from the side upper surface of the tire can be received (an imaging position) during imaging, as illustrated in FIGS. 5, 6, and 8. The second mirror 303 is positioned within the tire cavity region in the case where the second mirror 303 is positioned outside of the outer circumference of the inner surface measurement stage 11.

The third mirror 304 is affixed by a support member to a position, within the outer circumference of the inner surface measurement stage 11, where reflected slit light that has been reflected by the second mirror 303 can be reflected toward an incidence opening and furthermore a light-receiving surface of the camera 305. The third mirror 304 is a sub-mirror that is provided within an optical path of reflected light from the line irradiation region, between the camera 305 and the second mirror 303, and that directs the light reflected by the second mirror 303 toward the incidence opening and furthermore the light-receiving surface of the camera 305.

The camera 305 is attached, via a mobile mechanism unit 308, to an anchor column affixed perpendicular to the inner surface measurement stage 11. The camera 305 is a side inner surface camera that images the line irradiation region on the tread inner surface from a direction tilted in the tire circumferential direction via the second mirror 303 and outputs image data. Additionally, the camera 305 includes a fixed focus lens, and the focus of the image of the line irradiation region is adjusted by varying a distance along the optical path between the lens of the camera 305 and the third mirror 304, and furthermore, the second mirror 303, using the mobile mechanism unit 308 along the anchor column. For example, the distance along the optical path between the line irradiation region and the camera 305 can be made constant regardless of the outer diameter of the tire.

The mobile mechanism unit 308 is operated by a stepping motor, and the driving of the stepping motor is controlled by the computer device, which will be described later.

Next, an electrical control system of the device 1 will be described.

Figure 13:
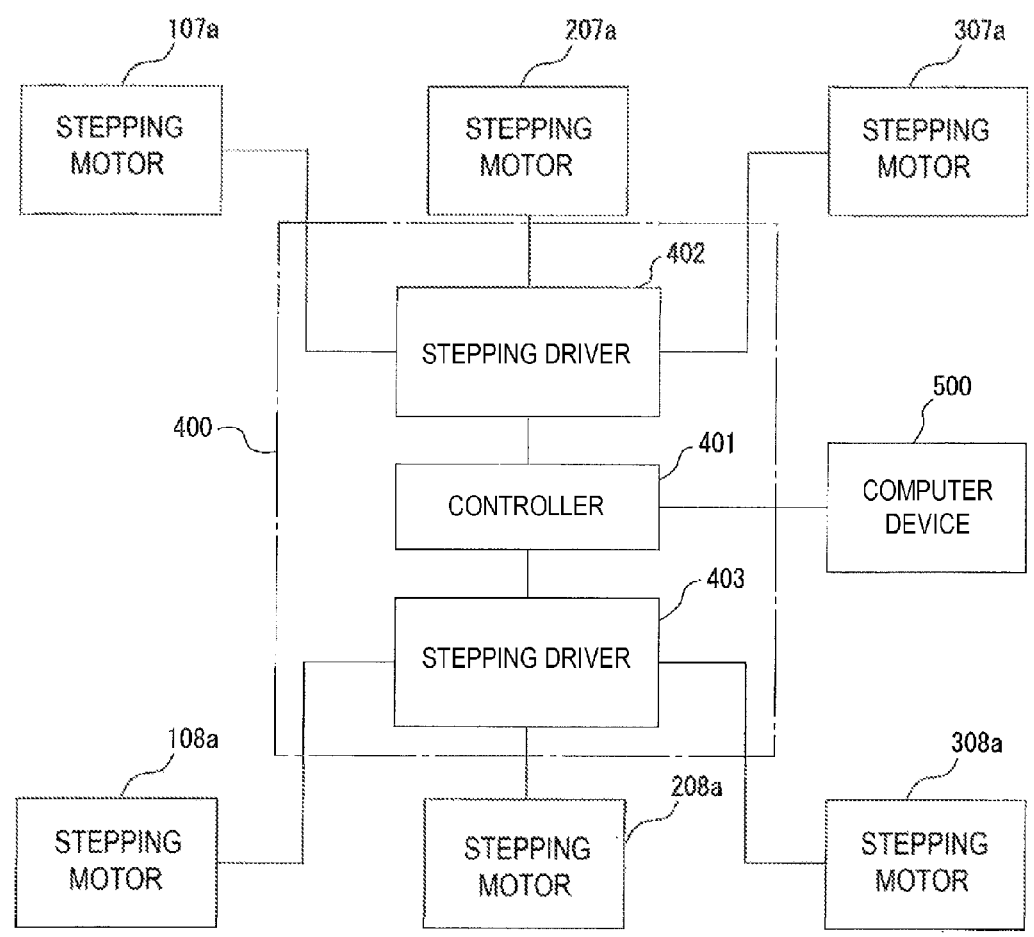
FIG. 13 is a block diagram illustrating an electrical control system according to the embodiment of the present technology.

As illustrated in FIG. 13, driving of stepping motors 107*a*, 207*a*, and 307*a* of the rotational driving mechanism units 107, 207 and 307 and stepping motors 108*a*, 208*a*, and 308*a* of the mobile mechanism units 108, 208, and 308 in the respective above-described optical systems is controlled by a computer device 500 via a control signal distribution unit 400. In other words, the control signal distribution unit 400 is constituted by a controller 401 and two stepping drivers 402 and 403.

A control signal for driving, output from the computer device 500, is input into the controller 401, and control signals are distributed to the stepping driver 402, which is for the rotational driving mechanism units, and to the stepping driver 403, which is for the mobile mechanism units, by the controller 401. The computer device 500 is a control unit that controls the revolution of the second mirror 203, which is a tread inner surface mirror affixed to the support member 206, by controlling the rotation amount of the rotation shaft of the support member 206. More specifically, the computer device 500 is configured to generate a control signal for the rotation amount of the above-described rotation shaft according to the outer diameter of the tire so that, when the second mirror 203 is revolved and inserted into the tire cavity region to be set in the imaging position, a tilt angle for imaging the line irradiation region by the camera 205 is within an acceptable range. Likewise, the second mirrors 103 and 303 revolve around the rotation shafts of the support members 106 and 306 so as to be inserted into the tire cavity region while varying their orientations. At this time, the device 1 is in a state of being inserted into the opening 2*a* of the tire, with the rotation shaft around which the second mirror 203 revolves being parallel to the central axis of rotation of the tire and the rotation shaft being offset relative to the central axis of rotation of the tire. The stepping driver 402 generates driving signals for driving the stepping motors 107*a*, 207*a*, and 307*a* of the respective rotational driving mechanism units 107, 207 and 307 on the basis of the control signal sent from the computer device 500 via the controller 401, and outputs the driving signals to the stepping motors 107*a*, 207*a*, and 307*a*. The stepping driver 403 generates driving signals for driving the stepping motors 108*a*, 208*a*, and 308*a* of the respective mobile mechanism units 108, 208, and 308 on the basis of the control signal sent from the computer device 500 via the controller 401, and outputs the driving signals to the stepping motors 108*a*, 208*a*, and 308*a*.

Next, operations for imaging the tire inner surface with the device 1 will be described.

As illustrated in FIGS. 2 to 4, when the tire inner surface is imaged, the support column 12 positioned in the center of the inner surface measurement stage 11 is caused to match a central axis of rotation of the tire 2, and the inner surface measurement stage 11 is then inserted into the opening 2a of the tire 2, in a state where the second mirrors 103, 203, and 303 of the respective optical systems 100 to 300 are retracted, or in other words, in a state where the second mirrors 103, 203, and 303 are positioned within the outer circumference of the inner surface measurement stage 11. Therefore, the device 1 does not interfere with the bead base region that surrounds the opening 2a of the tire 2. Subsequently, the second mirrors 103, 203, and 303 of the optical systems 100 to 300 are revolved and extended. Furthermore, after slit light is emitted from the light sources 101, 201, and 301 of the respective optical systems 100 to 300 and the positions of the cameras 105, 205, and 305 are adjusted by driving the mobile mechanism units 108, 208, and 308, the device 1 or the tire 2 is rotated once in the tire circumferential direction while an external device obtains the image data output from all of the cameras 105, 205, and 305 of the respective optical systems 100 to 300.

Accordingly, it is only necessary to insert the second mirrors 103, 203, and 303 of the respective optical systems 100, 200, and 300 into the tire cavity region, which is the interior of the tire 2, making it possible to reduce the size of the portion to be inserted into the tire cavity region compared to conventional configurations. As a result, the three optical systems 100, 200, and 300 for imaging the entire inner surface of the tire 2 can be driven simultaneously.

Additionally, the entire tire inner surface can be imaged over a single pass in the circumferential direction of the tire simply by rotating the device 1 or the tire 2 once in the tire circumferential direction. Accordingly, the amount of time required to image the entire tire inner surface can be greatly shortened compared to conventional configurations.

Next, operations carried out by each of the optical systems 100, 200, and 300 during imaging will be described.

Figure 14:
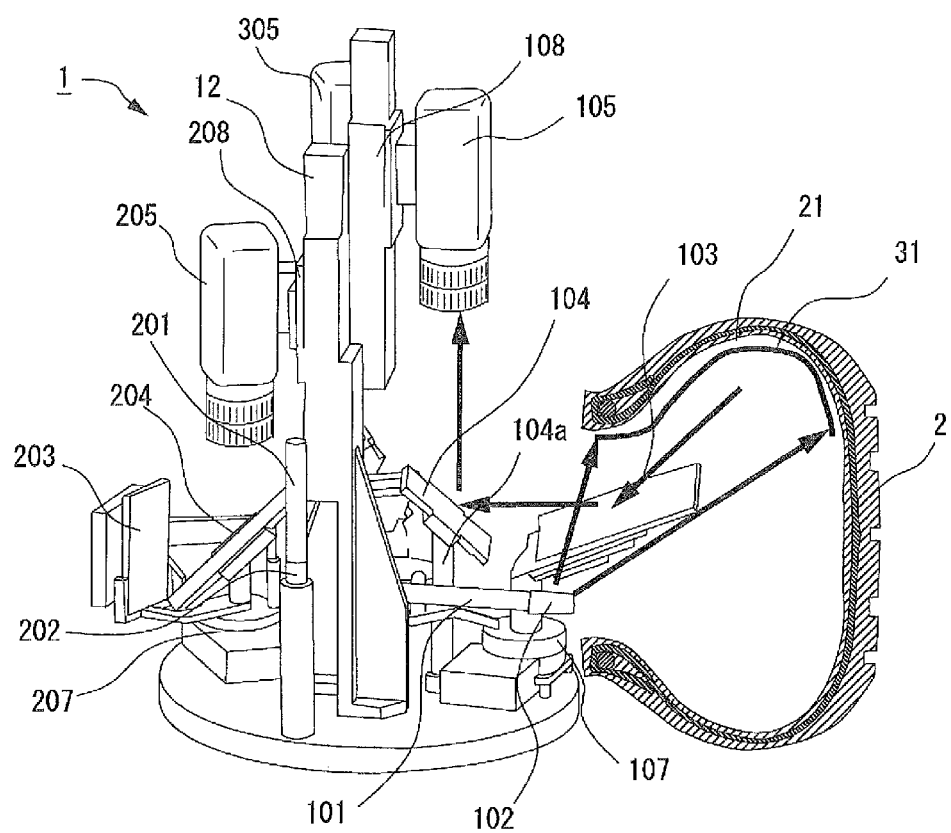
FIG. 14 is a perspective view illustrating operations performed when a tire inside upper surface is imaged according to the embodiment of the present technology.
Figure 15:
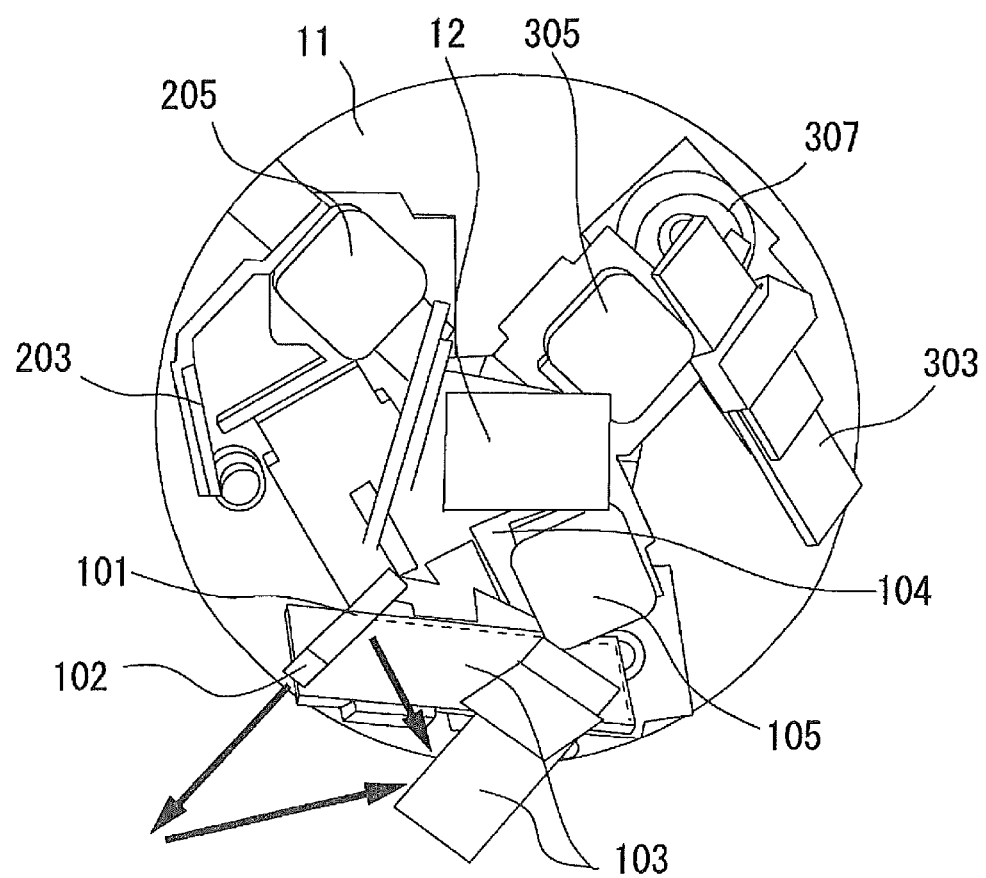
FIG. 15 is a plan view illustrating operations performed when the tire inside upper surface is imaged according to the embodiment of the present technology.

First, with respect to the first optical system 100, the inner surface measurement stage 11 is inserted into a predetermined position within the tire from the opening of the tire 2, and the second mirror 103 is then revolved and extended in the tire 2, as illustrated in FIGS. 14 and 15. In this state, slit light is emitted from the light source 101, and the position of the camera 105 is adjusted by driving the mobile mechanism unit 108.

The slit light emitted from the light source 101 is reflected by the first mirror 102 and illuminates a side upper surface 21 of the tire 2, forming a line irradiation region 31. The slit light reflected by the side upper surface 21 is incident on the second mirror 103, and is reflected toward the third mirror 104 by the second mirror 103. The slit light incident on the third mirror 104 is reflected by the third mirror 104 toward the incidence opening and furthermore the light-receiving surface of the camera 105.

Figure 16:
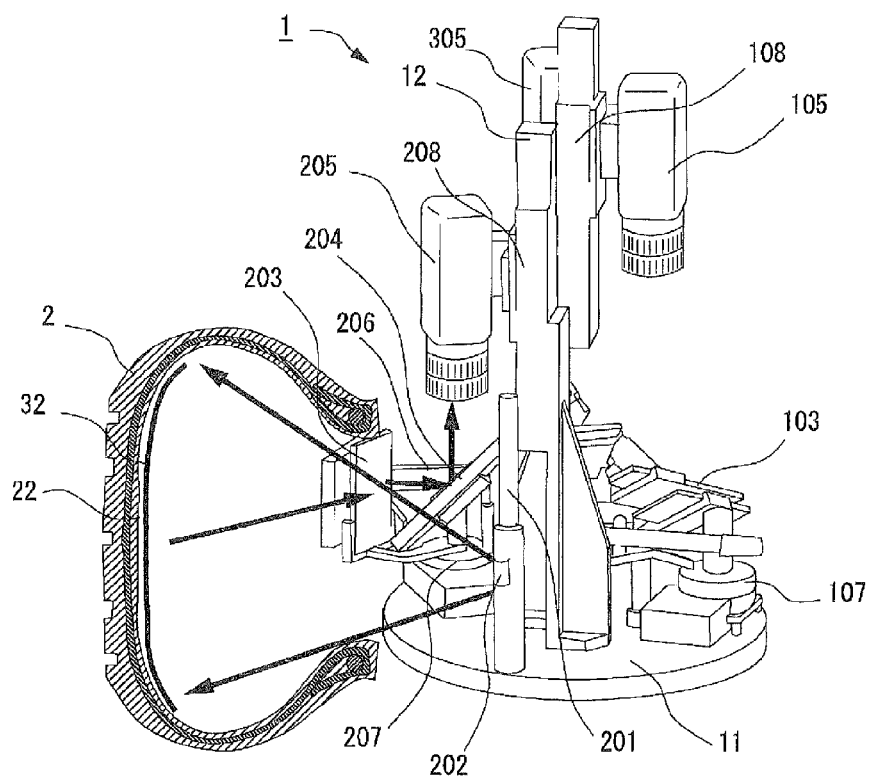
FIG. 16 is a perspective view illustrating operations performed when a tire tread inner surface is imaged according to the embodiment of the present technology.
Figure 17:
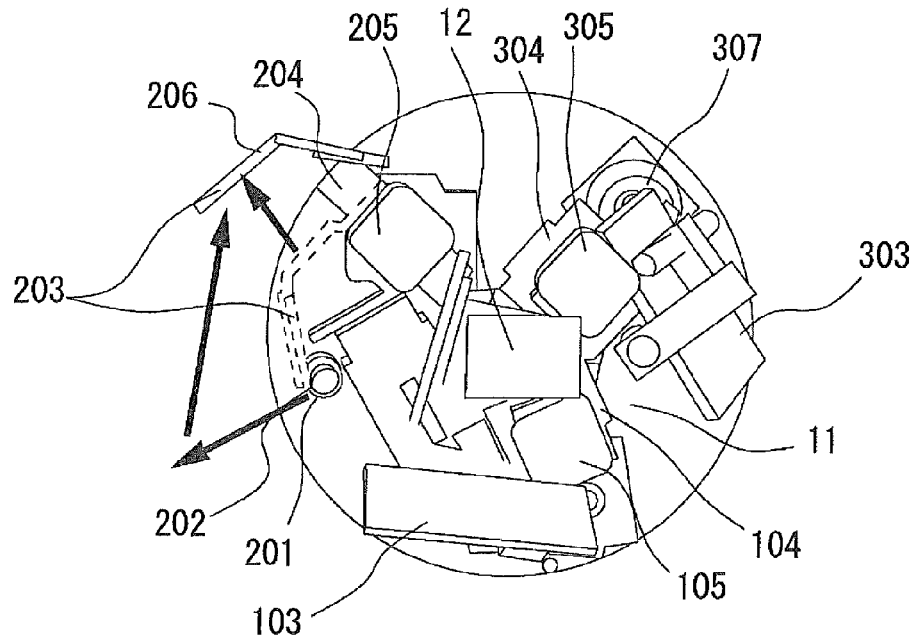
FIG. 17 is a plan view illustrating operations performed when the tire tread inner surface is imaged according to the embodiment of the present technology.

With respect to the second optical system 200, the inner surface measurement stage 11 is inserted into a predetermined position within the tire from the opening of the tire 2, and the second mirror 203 is then revolved and extended in the tire, as illustrated in FIGS. 16 and 17. In other words, starting from a first position in which the second mirror 203 is located so that the outer circumference of the portion of the device 1 to be inserted into the opening of the tire is smaller than the inner circumference of the tire, the second mirror 203 is revolved in accordance with a determined rotation amount to be located in an imaging position. In this state, slit light is emitted from the light source 201, and the position of the camera 205 is adjusted by driving the mobile mechanism unit 208.

The slit light emitted from the light source 201 is reflected by the first mirror 202 and illuminates a tread inner surface 22 of the tire 2, forming a line irradiation region 32. The slit light reflected by the tread inner surface 22 is incident on the second mirror 203, and is reflected toward the third mirror 204 by the second mirror 203. The reflected light incident on the third mirror 204 is reflected by the third mirror 204 toward the incidence opening and furthermore the light-receiving surface of the camera 205.

Figure 18:
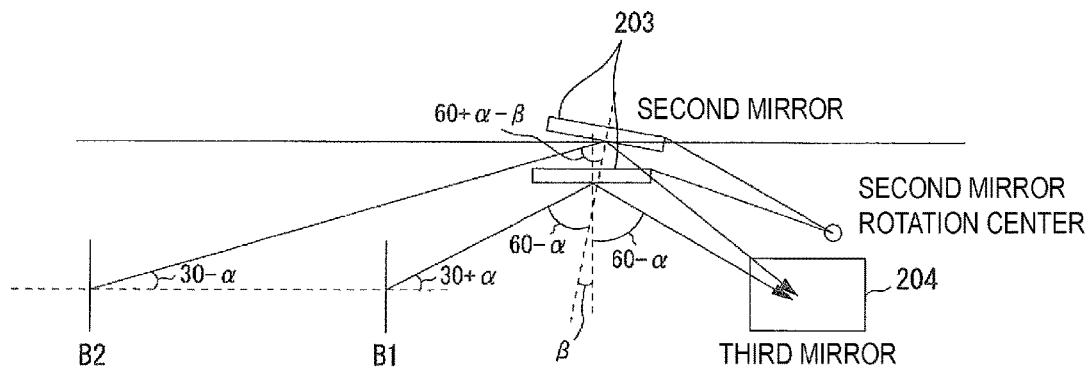
FIG. 18 is a diagram illustrating a relationship between a rotational position of a second mirror and a tire inner surface when the tire tread inner surface is imaged.

Additionally, as illustrated in FIG. 18, the second mirror 203 reflects an image of the line-form irradiation region, formed by the slit light, on the tread inner surface to the third mirror 204, the image corresponding to a field of view taken from a direction tilted approximately 30 degrees in the tire circumferential direction. In other words, the camera 205 images the line irradiation region from a direction tilted in the tire circumferential direction via the second mirror 203 and outputs image data. The rotational driving mechanism unit 207 revolves the second mirror 203 around the rotation shaft, bringing the tilt angle of the imaging of the line irradiation region on the tread inner surface 22 within an acceptable range, which is, for example, a range of approximately 30 degrees, more specifically a range of 30 degrees $\pm\alpha$. Within this range, the line irradiation region can be imaged from a minimum diameter tread inner surface B1 to a maximum diameter tread inner surface B2. In other words, in the drawing, an angle of reflection at the minimum diameter tread inner surface B1 is $30+\alpha$ degrees, and an angle of incidence and angle of reflection at the second mirror 203 is $60-\alpha$ degrees as this time. Additionally, an angle of reflection at the maximum diameter tread inner surface B2 is $30-\alpha$ degrees, and an angle of incidence and angle of reflection at the second mirror 203 is $60+\alpha-\beta$ degrees as this time. When the tilt angle of the imaging of the line irradiation region is reduced, the image formed by imaging the line irradiation region increasingly deforms from a straight line, extending outside the range of the field of view of the second mirror 203. However, because the second mirror 203 is inserted into the tire cavity region, the size of the second mirror is limited and cannot be increased. On the other hand, if the tilt angle of the imaging of the line irradiation region is increased, the resolution of shape data obtained through processing based on the light section method will drop. Therefore, the acceptable range is set to $30\pm\alpha$ degrees in the present embodiment. Here, it is preferable that $\alpha$ be an angle of no more than 5 degrees, for example. Although the median in the above-described acceptable range is 30 degrees in the present embodiment, it is preferable that the median be an angle within a range of 25 to 35 degrees.

Figure 19:
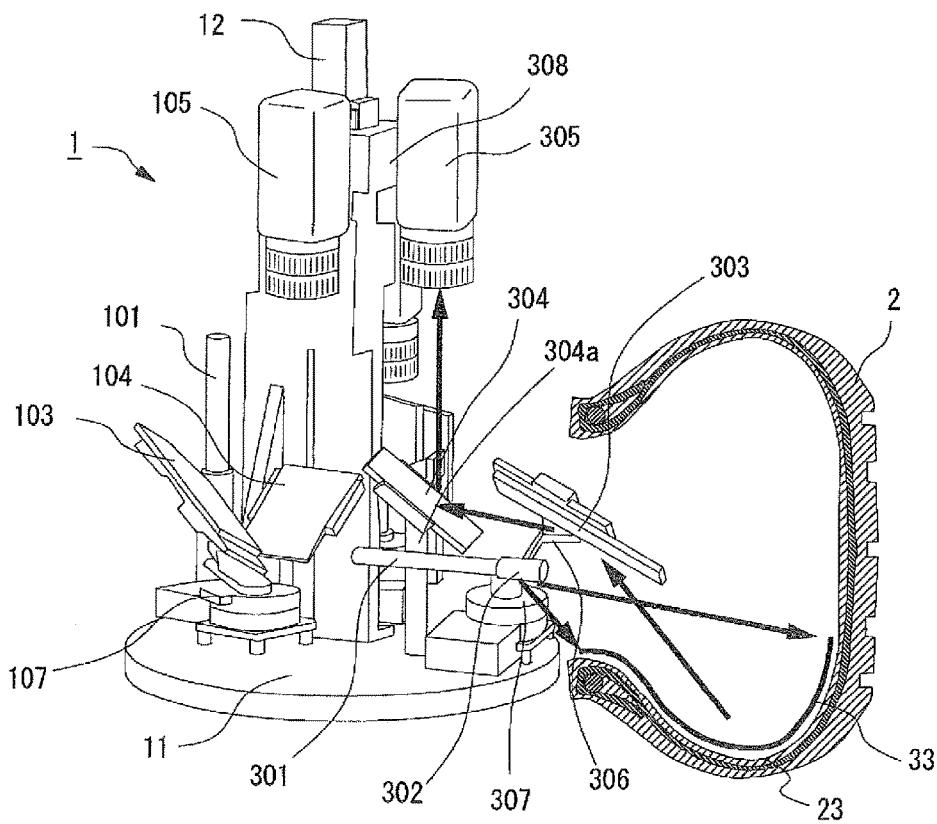
FIG. 19 is a perspective view illustrating operations performed when a tire inside lower surface is imaged according to the embodiment of the present technology.
Figure 20:
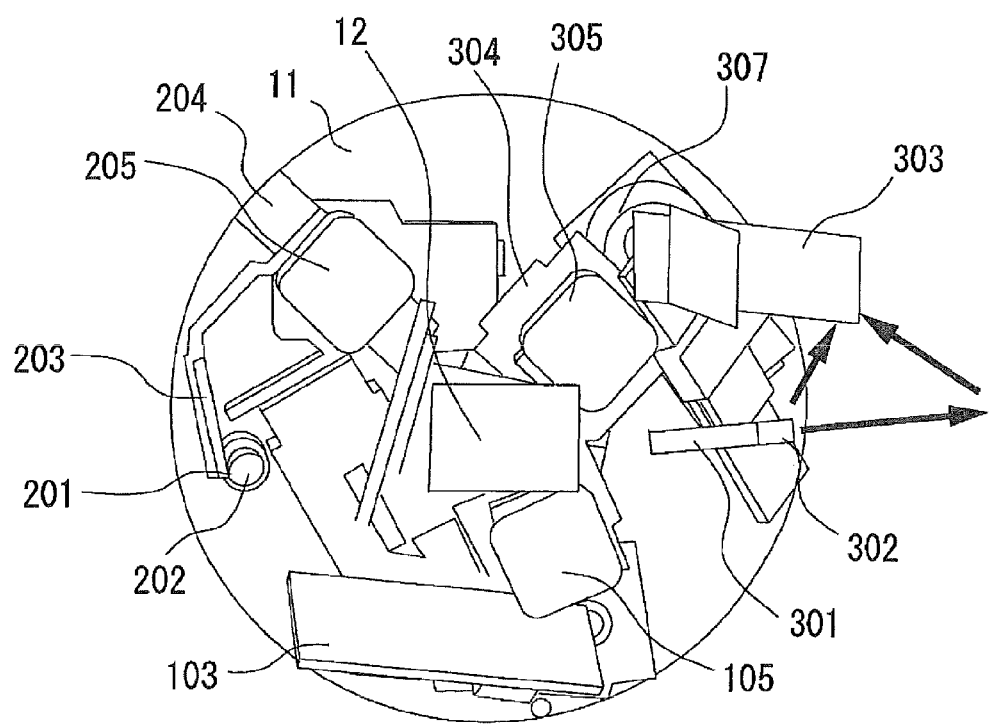
FIG. 20 is a plan view illustrating operations performed when the tire inside lower surface is imaged according to the embodiment of the present technology.

With respect to the third optical system 300, the inner surface measurement stage 11 is inserted into a predetermined position within the tire from the opening of the tire 2, and the second mirror 303 is then revolved and extended in the tire, as illustrated in FIGS. 19 and 20. In this state, slit light is emitted from the light source 301, and the position of the camera 305 is adjusted by driving the mobile mechanism unit 308.

The slit light emitted from the light source 301 is reflected by the first mirror 302 and illuminates a side lower surface 23 of the tire 2, forming a line irradiation region 33. The slit light reflected by the side lower surface 23 is incident on the second mirror 303, and is reflected toward the third mirror 304 by the second mirror 303. The reflected light incident on the third mirror 304 is reflected by the third mirror 304 toward the incidence opening and furthermore the light-receiving surface of the camera 305.

Figure 21:
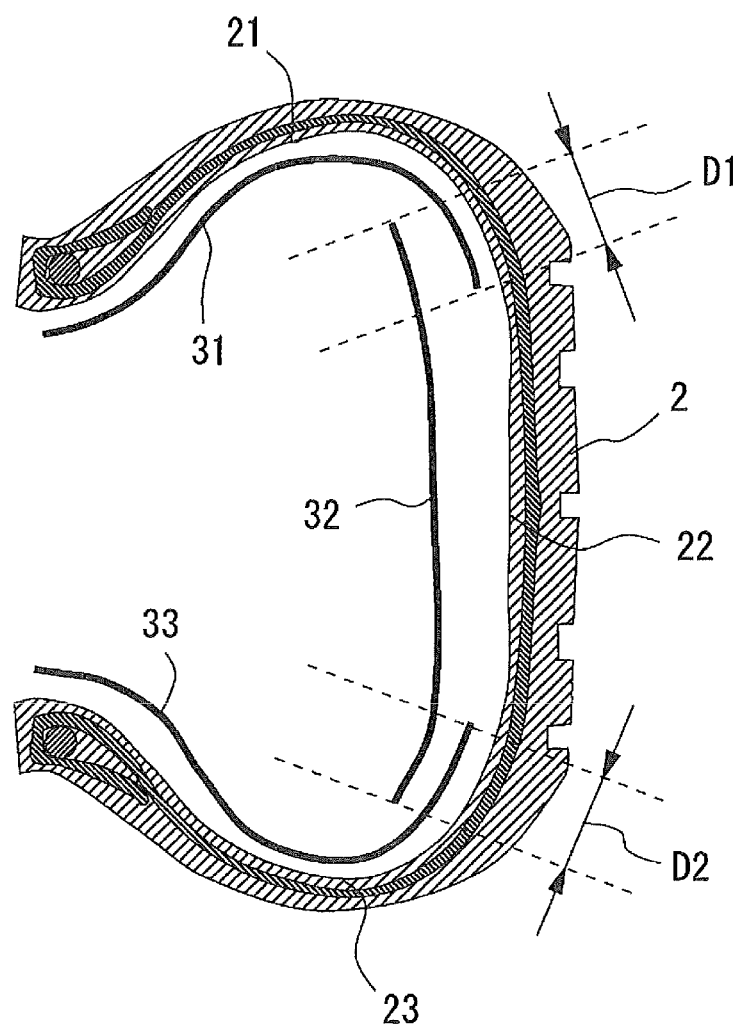
FIG. 21 is a diagram illustrating a relationship between imaging regions of respective optical systems according to the embodiment of the present technology.

Note that in the present embodiment, the respective imaging ranges of the adjacent line irradiation regions 31, 32, and 33 are set so as to partially overlap in the tire width direction or a tire radial direction, as illustrated in FIG. 21. In other words, the line irradiation region 31 on the side upper surface 21 and the line irradiation region 32 on the tread inner surface 22 overlap one another by a width D1. Likewise, the line irradiation region 32 on the tread inner surface 22 and the line irradiation region 33 on the side lower surface 23 overlap one another by a width D2. This configuration prevents any region from not being imaged. In the present embodiment, the widths D1 and D2 are set to no less than 10 mm.

According to the tire inner surface imaging method and device of the present embodiment as described thus far, the optical systems 100, 200, and 300 are provided for each of the portions obtained by dividing the inner surface of the tire 2 into three portions in the width direction. This configuration allows the tire inner surface to be scanned with the slit light along the tire circumferential direction by rotating at least the tire 2 or the imaging device 1 once in the tire circumferential direction central to the axis of the tire 2. As a result, the entire tire inner surface can be imaged over a single pass in the circumferential direction of the tire. Accordingly, the amount of time required to image the entire tire inner surface can be greatly shortened compared to conventional configurations.

Accordingly, it is only necessary to insert the inner surface measurement stage 11 and the second mirrors 103, 203, and 303 of the respective optical systems 100, 200, and 300 into the tire 2, making it possible to reduce the size of the portion to be inserted into the tire 2 compared to conventional configurations. As a result, the three optical systems 100, 200, and 300 for imaging the entire inner surface of the tire 2 can be driven simultaneously.

Additionally, according to the present embodiment, the second mirrors 103, 203, and 303 can be revolved to different positions, and furthermore the cameras 105, 205, and 305 can be moved to different positions. As such, the entire tire inner surface can be imaged even if a tire 2 to be imaged is replaced with another tire 2 and the size of the tire, or in other words, the outer diameter of the tire, changes to some extent. In the present embodiment, the positions of the second mirrors 103, 203, and 303 in an extended state, or in other words, the imaging positions, are stored in advance for each of the outer diameters of tires. Thus, setting the outer diameter of a tire in the computer device 500 enables the second mirrors 103, 203, and 303 to be positioned to the imaging positions.

Although the inner surface of the tire 2 is divided into three regions in the present embodiment, namely the side upper surface 21, the tread inner surface 22, and the side lower surface 23, it should be noted that it is preferable that the number of the regions be changed depending on the size of the tire 2 and an optical system be provided for each of the regions. The diameter of the opening 2a of the tire 2 increases as the size of the tire 2 increases, and thus the diameter of the inner surface measurement stage 11 can be increased; as a result, the inner surface measurement stage 11 can be disposed in a division obtained by dividing the outer circumference of the inner surface measurement stage 11 at angles no greater than 120 degrees, which makes it possible to provide the inner surface measurement stage 11 with three or more optical systems. For example, in the case where the tire is large, the side upper surface 21 may be divided into multiple regions, the tread inner surface 22 may be divided into multiple regions, and the side lower surface 23 may be divided into multiple regions, and so on.

Additionally, the positions of the light sources 101, 201, and 301 and the cameras 105, 205, and 305 are not limited to the positions described in the present embodiment, and the arrangements thereof can be changed by changing the angles of the mirrors.

Additionally, light sources that emit laser sheet light may be employed as the light sources 101, 201, and 301 that emit slit light.

Additionally, although stepping motors are used to revolve the second mirrors 103, 203, and 303 and to move the cameras 105, 205, and 305 in the present embodiment, the technology is not limited to this configuration.

The present technology relates to a tire inner surface imaging method and device capable of imaging the overall inner surface of a tire in a short amount of time.

The invention claimed is:

1. A tire inner surface imaging method for imaging a tire inner surface, the method comprising the steps of:
    setting a mirror in an imaging position by revolving the mirror around a rotation shaft so that the mirror is inserted into a tire cavity region with a portion of an imaging device inserted into an opening of a tire, the imaging device including a light source, the mirror, and a camera and being configured so that the mirror revolves around the rotation shaft while an orientation of a surface of the mirror changes;
    scanning a tread inner surface of the tire with slit light by irradiating the tread inner surface with the slit light; and
    outputting image data generated by the camera imaging a line irradiation region on the tread inner surface from a direction tilted with respect to a tire circumferential direction via the mirror during the scanning with the slit light, the line irradiation region being formed through the irradiation of the slit light,
    a rotation amount of the rotation shaft, when the mirror is inserted into the tire cavity region, being determined according to an outer diameter of the tire so that an angle of tilt of the imaging performed by the camera is within an acceptable range.

2. The tire inner surface imaging method according to claim 1, wherein the camera is a fixed focus camera, and a mechanism that changes a distance of an optical path between the mirror and the camera is provided.

3. The tire inner surface imaging method according to claim 1, wherein the step of setting the mirror in the imaging position includes revolving the mirror to the imaging position according to the rotation amount determined for the mirror, from a position in which the mirror is located so that an outer circumference of a portion of the imaging device to be inserted into the opening is smaller than an inner circumference of the tire.

4. The tire inner surface imaging method according to claim 1, wherein a sub-mirror is provided in an optical path, between the camera and the mirror, of light reflected from the line irradiation region, the sub-mirror being configured to direct light reflected by the mirror toward a light-receiving surface of the camera.

5. The tire inner surface imaging method according to claim 1,
    wherein the imaging device includes a side inner surface imaging optical system besides a tread inner surface imaging optical system that includes the light source, the mirror, and the camera as a tread inner surface light source, a tread inner surface mirror, and a tread inner surface camera, respectively, the side inner surface imaging optical system configured to output image data generated by a side inner surface camera imaging, from a direction tilted in the tire circumferential direction via a side inner surface mirror, a line irradiation region formed by irradiating a side inner surface of the tire inner surface with slit light emitted from a side inner surface light source, the side inner surface mirror being configured to revolve around a side inner surface rotation shaft while an orientation of the side inner surface mirror changes; and the step of setting the mirror in the imaging position includes revolving the side inner surface mirror so that the side inner surface mirror is inserted into the tire cavity region.

6. A tire inner surface imaging device that images a tire inner surface, the device comprising:
a light source configured to irradiate a tread inner surface of a tire with slit light;
a mirror configured to reflect light reflected from a line irradiation region on the tread inner surface formed by the irradiation of the slit light;
a camera configured to output image data generated by receiving light reflected by the mirror and imaging the line irradiation region from a direction tilted in a tire circumferential direction;
an inner surface measurement stage where the light source, the mirror, the camera, and a mechanism are mounted, the mechanism being configured to revolve the mirror around a rotation shaft while changing an orientation of a surface of the mirror, the inner surface measurement stage having an outer circumference smaller than an inner circumference of an opening of the tire; and
a control unit configured to control revolution of the mirror by controlling a rotation amount of the rotation shaft, the control unit being configured to generate a control signal for the rotation amount of the rotation shaft according to an outer diameter of the tire so that, when the mirror is revolved around the rotation shaft and inserted into a tire cavity region to be se in an imaging position with a portion of the imaging device inserted into an opening of the tire, an angle of tilt of the imaging of the line irradiation region performed by the camera is within an acceptable range.

7. The tire inner surface imaging device according to claim 6, wherein the camera is a fixed focus camera, and a mechanism configured to move the camera so as to change a distance of an optical path between the mirror and the camera is provided.

8. The tire inner surface imaging device according to claim 6, wherein the control unit uses the control signal to revolve the mirror from a position in which the mirror is located so that the outer circumference of the inner surface measurement stage is smaller than an inner circumference of the tire.

9. The tire inner surface imaging device according to claim 6, wherein a sub-mirror is provided in an optical path, between the camera and the mirror, of light reflected from the line irradiation region, the sub-mirror being configured to direct light reflected by the mirror toward a light-receiving surface of the camera.

10. The tire inner surface imaging device according to claim 6, further comprising a side inner surface imaging optical system besides a tread inner surface imaging optical system that includes the light source, the mirror, and the camera as a tread inner surface light source, a tread inner surface mirror, and a tread inner surface camera, respectively, the side inner surface imaging optical system including a side inner surface light source configured to irradiate a side inner surface of the tire inner surface with slit light, a side inner surface camera configured to output image data generated by imaging a line irradiation region formed by the irradiation of the slit light, and a side inner surface mirror that is provided in an optical path of light reflected from the line irradiation region so that the side inner surface camera performs the imaging from a direction tilted in the tire circumferential direction, the side inner surface mirror being configured to revolve around a side inner surface rotation shaft while an orientation of the side inner surface mirror changes.

11. The tire inner surface imaging method according to claim 2, wherein the step of setting the mirror in the imaging position includes revolving the mirror to the imaging position according to the rotation amount determined for the mirror, from a position in which the mirror is located so that an outer circumference of a portion of the imaging device to be inserted into the opening is smaller than an inner circumference of the tire.

12. The tire inner surface imaging method according to claim 11, wherein a sub-mirror is provided in an optical path, between the camera and the mirror, of light reflected from the line irradiation region, the sub-mirror being configured to direct light reflected by the mirror toward a light-receiving surface of the camera.

13. The tire inner surface imaging method according to claim 12,
wherein the imaging device includes a side inner surface imaging optical system besides a tread inner surface imaging optical system that includes the light source, the mirror, and the camera as a tread inner surface light source, a tread inner surface mirror, and a tread inner surface camera, respectively, the side inner surface imaging optical system configured to output image data generated by a side inner surface camera imaging, from a direction tilted in the tire circumferential direction via a side inner surface mirror, a line irradiation region formed by irradiating a side inner surface of the tire inner surface with slit light emitted from a side inner surface light source, the side inner surface mirror being configured to revolve around a side inner surface rotation shaft while an orientation of the side inner surface mirror changes; and the step of setting the mirror in the imaging position includes revolving the side inner surface mirror so that the side inner surface mirror is inserted into the tire cavity region.

14. The tire inner surface imaging device according to claim 7, wherein the control unit uses the control signal to revolve the mirror from a position in which the mirror is located so that the outer circumference of the inner surface measurement stage is smaller than an inner circumference of the tire.

15. The tire inner surface imaging device according to claim 14, wherein a sub-mirror is provided in an optical path, between the camera and the mirror, of light reflected from the line irradiation region, the sub-mirror being configured to direct light reflected by the mirror toward a light-receiving surface of the camera.

16. The tire inner surface imaging device according to claim 15, further comprising a side inner surface imaging optical system besides a tread inner surface imaging optical system that includes the light source, the mirror, and the camera as a tread inner surface light source, a tread inner surface mirror, and a tread inner surface camera, respectively, the side inner surface imaging optical system including a side inner surface light source configured to irradiate a side inner surface of the tire inner surface with slit light, a side inner surface camera configured to output image data generated by imaging a line irradiation region formed by the irradiation of the slit light, and a side inner surface mirror that is provided in an optical path of light reflected from the line irradiation region so that the side inner surface camera performs the imaging from a direction tilted in the tire circumferential direction, the side inner surface mirror being configured to revolve around a side inner surface rotation shaft while an orientation of the side inner surface mirror changes.

* * * * *

UNITED STATES PATENT AND TRADEMARK OFFICE
CERTIFICATE OF CORRECTION

PATENT NO. : 9,741,109 B2  
APPLICATION NO. : 15/118446  
DATED : August 22, 2017  
INVENTOR(S) : Hirotaro Tada, Masamichi Oyama and Tsutomu Yamamoto Page 1 of 1

It is certified that error appears in the above-identified patent and that said Letters Patent is hereby corrected as shown below:

On the Title Page

Item (72), the residence of the third inventor, Tsutomu Yamamoto, should be changed to Odawara (JP).

Signed and Sealed this
Twenty-first Day of August, 2018

Andrei Iancu
*Director of the United States Patent and Trademark Office*